United States Patent
Kloss-Ulitzka et al.

(10) Patent No.: US 6,770,243 B2
(45) Date of Patent: Aug. 3, 2004

(54) CHROME STEEL ALLOY

(75) Inventors: Gisbert Kloss-Ulitzka, Neuenrade (DE); Gunter Schnabel, Hagen (DE); Oskar Pacher, Graz (AT)

(73) Assignee: Stahlwerk Ergste Westig GmbH, Schwerte (DE)

( * ) Notice: Subject to any disclaimer, the term of this patent is extended or adjusted under 35 U.S.C. 154(b) by 0 days.

(21) Appl. No.: 10/181,299

(22) PCT Filed: Jan. 8, 2001

(86) PCT No.: PCT/EP01/00100
§ 371 (c)(1), (2), (4) Date: Jul. 17, 2002

(87) PCT Pub. No.: WO01/53555
PCT Pub. Date: Jul. 26, 2001

(65) Prior Publication Data
US 2003/0165394 A1 Sep. 4, 2003

(30) Foreign Application Priority Data
Jan. 17, 2000 (DE) .......................................... 100 01 725
Jun. 2, 2000 (DE) .......................................... 100 27 049

(51) Int. Cl.⁷ .......................... C22C 38/22; C22C 38/24; C22C 38/26; C22D 38/28
(52) U.S. Cl. ............................ 420/68; 420/69; 148/325
(58) Field of Search ................................. 148/325–326; 420/67–69

(56) References Cited

U.S. PATENT DOCUMENTS

| | | | |
|---|---|---|---|
| 5,364,588 A | * 11/1994 | Finkl et al. | 420/67 |
| 5,534,081 A | * 7/1996 | Takagi et al. | 148/325 |
| 5,641,453 A | 6/1997 | Hackl et al. | 420/42 |
| 5,651,843 A | * 7/1997 | Bendel et al. | 148/327 |

FOREIGN PATENT DOCUMENTS

| | | |
|---|---|---|
| DE | 3901470 C | 8/1990 |
| EP | 0 694 622 B1 | 1/1996 |
| EP | 0 694 622 A1 | 1/1996 |
| JP | 01275737 A | 11/1989 |
| JP | 4048050 A | 2/1992 |
| WO | 01/00100 | 4/2001 |

* cited by examiner

Primary Examiner—Deborah Yee
(74) Attorney, Agent, or Firm—Cook, Alex, McFarron, Manzo, Cummings & Mehler, Ltd.

(57) ABSTRACT

A chromium steel alloy having 0.4 to 0.75% of carbon, 0.4 to 1.6% of manganese, 12 to 19% of chromium, up to 0.2% of nickel, up to 0.7% of silicon, 0.5 to 1.5% of molybdenum, up to 1.5% of tungsten, 0.05 to 0.3% of vanadium and (% Ti/% Nb), 0.02 to 0.15% of sulfur, up to 0.1% of nitrogen and up to 0.008% of boron, remainder iron including smelting-related impurities. This steel alloy is distinguished by good processability, resistance to corrosion, resistance to abrasion, a high resistance to heat up to 300° C. and above, and a high rigidity.

11 Claims, 1 Drawing Sheet

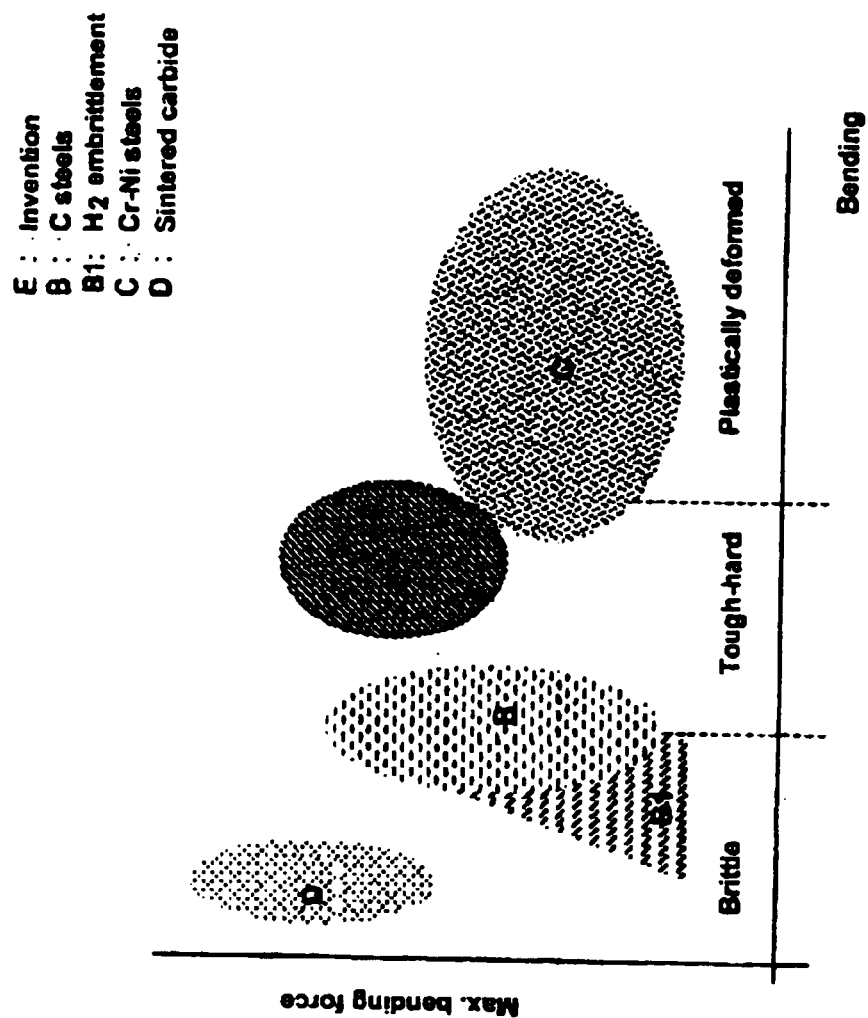

CHROME STEEL ALLOY

Recent developments in sewing machines have also decisively changed the profile of demands imposed on industrial (sewing) needles. Hitherto, industrial needles for sewing machines have been produced from a carbon steel containing approximately 0.8 to 1.1% of carbon. In humid air, needles of this type tend to form rust spots, which very greatly limits their use. Therefore, to improve the resistance to corrosion and to avoid the formation of rust, the needles are coated by electrodeposition, for example in rotating drums. Nickel and/or chromium is applied as coating by cathode deposition. The layer thicknesses often differ very considerably, and critical areas, for example in the region of the eye, the point or the thread groove, can often only be provided with a very thin coating. However, it is in these very regions that, in operation, high levels of wear occur. Abrasion of the coating is also undesirable, since it is known that nickel is a highly allergenic metal even in very small concentrations.

A further drawback of the coating by electrodeposition is that during cathode deposition of metal in electrodeposition baths, hydrogen can be incorporated in the needle material. This hydrogen causes the brittleness to increase very considerably, with the result that there is a risk of needles breaking, with possible damage to the machine.

For economic production of the needles, the workability is a parameter of crucial importance. This applies in particular to the production of thin needles. The carbon steels containing up to 1.1% of carbon which have been used hitherto are just able to satisfy these conditions, but in the annealed state with carbon contents of over 1% there may already be difficulties with working the thread groove and the eye. With these carbon steels, it is possible to achieve a hardness of at most 800 to 840 HV1 after a special heat treatment.

However, the temperature stability, i.e. the maintenance of the hardness after heating, is insufficient. Even in the case of heating to 300° C., a drop in hardness of more than 200 HV1 units (10 HRC units) is possible. Furthermore, at full hardness, there is a considerable susceptibility to uptake of hydrogen, for example during coating by electrodeposition. Even low hydrogen contents may embrittle the martensitic microstructure, which is stabilized only by carbon, and cause an increased risk of fractures. This is particularly critical in the case of thin needles. Because of difficulties in the micromachining and precision machining of the eye and the thread groove and because of insufficient matching of the alloying elements, it has hitherto been impossible to utilize the advantages of relatively high-alloy steels.

The demands imposed on new needle materials are determined primarily by the increases in performance in sewing machines. Developments are toward an increase in the economic viability of the production of seams combined, at the same time, with simple operation and a longer service life of the sewing machines. The following measures serve this purpose:

increasing the sewing speed,
improving the thread guidance,
optimizing the sewing foot pressure,
continuous adjustability of the stitch width,
highest possible stitching force of the needles combined with lowest possible friction.

The desire for higher sewing speeds results solely from economic considerations, in order to reduce costs and increase production. For example, industrial sewing machines are currently already driven at more than 7000 rpm. The high sewing speeds (i.e. the high stitch numbers) lead to particular loads on the needles and require adjustment of the materials and of the materials properties.

The high sewing speeds and the associated particular loads on the needles therefore require improved materials properties. These relate to the heat resistance of the needle point, the wear resistance as a sum property of corrosion and abrasion resistance, the hardness, the rigidity, the maximum bending force and the maximum bending.

Recent tests have shown that when thick materials are being sewn at high sewing speeds, temperatures of up to 300° C. occur at the needle point. Under these conditions, the wear resistance is significantly reduced after even a short period of use, a fact which is also attributable to insufficient protection by coatings applied by electrodeposition.

A major drawback of needles made from carbon steel is in particular the drop in the core hardness and the insufficient mechanical properties under extreme loads. The matrix, which is only stabilized by carbon, is often unable to resist deformation at elevated temperatures. As a result, the service life of the needle is reduced considerably. The deformation in turn significantly increases the risk of damage to the sewing machine.

An industrial needle should have a high core hardness and a high heat resistance, if possible to over 300° C.

The wear resistance as a sum property of abrasion resistance and corrosion resistance should be good and as far as possible should not be adversely affected by the action of air and moisture and by contact with abraded fabric and fibers (finishing agents, dyes, chemicals, bleach residues and other substances).

The risk of a needle breaking should also be low when different materials are being sewn, in particular during sewing in the transition region between different materials and when sewing padding and reinforcements.

The numerical value of the rigidity S, expressed as a quotient $F_{max}/S_{max}$ (maximum bending force/maximum bending) should be high and have a scatter which is as low as possible. The bending of a needle until it breaks should be between 1.5 and 2.5 mm and should not exceed 3.0 mm.

The production of needles should be inexpensive, environmentally friendly and simple. The shaping and heat treatment should be possible with conventional installations. In the case of needles made from sintered carbide (German laid-open specification 38 19 481), this condition is not satisfied, since shaping requires diamond grinding tools and the eye has to be manufactured by means of spark erosion.

Needles for medium sewing speeds are produced from wire, which has a simple alloy structure and is easy to process. Inexpensive production is a crucial aspect in the selection of the materials. Carbon steels containing approx. 0.8 to 1.1% of carbon, approximately corresponding to a steel with materials number 1.1545, are customary. For high demands on the needles, wire from the upper carbon range is currently used. However, the limits of processability are encountered in this range.

To produce an industrial needle, a wire is processed predominantly by means of chipless shaping. In this case, first of all the needle stem and neck are processed and extruded by means of presses, and the eye is flattened and shaped out. Then, the needles are straightened and the thread groove is introduced by means of roll stamping. Precision machining of the eye and sharpening of the needle point follow as further processing stages. There then follows a hardening step with a subsequent tempering treatment, if appropriate also in combination with a deep cooling treatment. The sewing needles then achieve a hardness of approx.

60 HRC. This is followed by precision grinding of the needle points, cleaning and coating with nickel and/or chromium by electrodeposition. The coating by electrodeposition takes place in rotating plastic vessels with direct current being supplied, the negative supply conductor being introduced into the interior of the plastic vessel, where it makes contact with the needles. The electrolyte used is often the acid solution of a chromate ($Cr^{6+}$) salt. From this solution, a thin film of chromium or hard chromium is deposited on a nickel layer which has often been deposited beforehand.

During the coating operation, it is very easy for hydrogen to diffuse into the lattice of the needle material, with the result that the hardened carbon steel can suffer considerable embrittlement. This in turn leads to a high susceptibility to breaking on the part of the needle and increases the risk of failure at high sewing speeds.

The drawback of hydrogen embrittlement can be avoided by using a physical coating process, for example the PVD (Physical Vapor Deposition) process. These processes predominantly operate in vacuum or at reduced pressure and require temperatures of 300 to 500° C. However, the relatively high temperatures lead to excessive thermal loads being placed on the needles—on account of their low content of alloying metals—and to a drop in the substrate hardness (core hardness). As a result, the compressive strength of the point deteriorates.

To achieve the highest possible compressive strength and hardness, German laid-open specification 38 19 481 proposes producing the needle stem and the point of a machine needle from an ultrafine-grained sintered carbide. This high-strength needle stem is to be joined to the needle shank by means of cold extrusion, erosion taking place in order to form the thread groove and the eye. However, the high costs of this complex shaping and the considerable time required for erosion machining do not satisfy the criteria of economic mass production and therefore have also not gained acceptance in practice.

It has also already been attempted to use known stainless steels with additions of molybdenum and other alloying elements for the production of industrial needles. The intention was in particular to improve the resistance to corrosion. However, these needles made from conventional stainless steels were difficult to work and did not achieve the required surface hardness. Compared to the known carbon steels, in particular the lower rigidity combined, at the same time, with a high degree of plastic deformation was a considerable drawback.

Therefore, to increase the surface hardness, German laid-open specification 2 054 671 proposes produced machine needles from a stainless steel and subsequently hardening the parts which are exposed to wear by nitriding.

This embodiment too has failed to gain acceptance in practice, since the high nitriding temperatures cause distortion, and the layer, which is only a few pm thick, did not result in any improvement in the compressive strength. Correcting the distortion by means of a straightening operation is generally difficult to carry out, since it leads to incipient cracks forming in the layer and therefore to the formation of fracture points.

The invention is based on the object of proposing a nickel-free or low-nickel alloy for the production of rust-free and wear-resistant needles, in particular for industrial needles. The alloy has an improved processability, a rigidity which is improved in the hardened and heat-treated state, an improved heat resistance and an excellent resistance to abrasion and resistance to corrosion.

The alloy contains:

| | |
|---|---|
| 0.4 to 0.75 | % of carbon, |
| 0.4 to 1.6 | % of manganese, |
| 12 to 19 | % of chromium, |
| up to 0.2 | % of nickel, |
| up to 0.7 | % of silicon, |
| 0.5 to 1.5 | % of molybdenum, |
| up to 1.5 | % of tungsten, |
| 0.05 to 0.3 | % of vanadium, titanium and niobium, |
| 0.02 to 0.15 | % of sulfur, |
| up to 0.1 | % of nitrogen, |
| up to 0.008 | % of boron, | remainder iron and smelting-related impurities.

A preferred embodiment contains:

| | |
|---|---|
| 0.6 to 0.7 | % of carbon, |
| 17 to 19 | % of chromium, |
| 0.03 to 0.1 | % of silicon, |
| 0.5 to 0.8 | % of manganese, |
| up to 0.1 | % of nickel, |
| 1 to 1.5 | % of molybdenum. |

Furthermore, it is advantageous if the alloy—individually or in addition to one another—contains in each case at least 0.10% of silicon, 0.05% of tungsten, 0.01% of titanium and, in each case in total, 0.05% of vanadium and titanium and/or 0.05% of vanadium and niobium.

The alloy is preferably characterized by the following relationship:

$$K_1=30\times(\%C+\%N)/(\%Cr+\%Mo)=0.9 \text{ to } 1.25.$$

A further characterization of the alloy may be the matching of the sulfide-forming elements manganese, titanium to sulfur and carbon and nitrogen. Particularly advantageous properties are given within the following limits:

$$K_2=10\times\%S/(\%C+\%N)=0.35 \text{ to } 1.50$$

and/or $$K_3=(\%Mn+\%Ti)/\%S=5 \text{ to } 30.$$

These relationships characterize the interaction of the sulfur as a function of the total carbon and nitrogen and manganese and titanium content.

The following properties of the alloy are particularly advantageous:

Good processability with shaping tools, in particular by means of stamping and punching tools.

High resistance to corrosion as a result of the alloying elements chromium and molybdenum. The high resistance to corrosion makes it possible to dispense with expensive, environmentally polluting coating processes using electrodeposition (chromium plating).

Elimination of the hydrogen embrittlement which is possible during coating by electro-deposition. The uptake of hydrogen may cause different levels of embrittlement to the needles, with the result that the risk of fractures increases considerably.

High resistance to wear and abrasion and high hardness after a standard heat treatment (hardening).

The good resistance to wear and the required hardness are achieved by a high strength of the matrix and carbides and/or carbonitrides which are finely distributed therein. The mechanical properties of the matrix are determined predominantly by the level of dissolved alloying elements and can be adjusted by specially matching the chromium, molybdenum, carbon and nitrogen contents, preferably with a nickel content of less than 0.1%.

Low plastic deformability of the hardened needles combined, at the same time, with a low scatter in the bending force, the bending and the needle rigidity.

The needle rigidity is characterized by the ratio of the maximum bending force to the maximum bending. These values are determined by the ratio of the alloying elements manganese and titanium to sulfur and of carbon end nitrogen to chromium and molybdenum.

Low scatter in the values for the maximum bending, the maximum bending force and the needle rigidity.

The alloy contains little or no nickel and is therefore distinguished by a particularly low allergenic potential; it is therefore also suitable for medical needles, which are exposed to aggressive chemical cleaning agents and disinfectants at elevated temperatures.

However, the material according to the invention is also suitable for the production of other needles, such as industrial needles.

The invention is explained in more detail below with reference to exemplary embodiments.

TABLE I

| Alloy | % C | % Cr | % Ni | % Mn | % Mo | % N | % S | % Ti |
|---|---|---|---|---|---|---|---|---|
| A1 | 0.92 | 0.27 | <0.1 | 0.28 | 0.01 | 0.01 | 0.002 | 0 |
| A2 | 1.06 | 0.20 | <0.1 | 0.33 | 0.01 | 0.01 | 0.003 | 0 |
| A3 | 0.96 | 0.15 | <0.1 | 0.32 | 0.02 | <0.01 | <0.002 | 0 |
| E1 | 0.62 | 17.3 | <0.1 | 0.48 | 0.55 | 0.08 | 0.03 | 0.04 |
| E2 | 0.68 | 18.5 | <0.1 | 0.60 | 0.7 | 0.09 | 0.10 | 0.07 |

TABLE I-continued

| Alloy | % C | % Cr | % Ni | % Mn | % Mo | % N | % S | % Ti |
|---|---|---|---|---|---|---|---|---|
| E3 | 0.60 | 18.7 | <0.1 | 0.65 | 0.65 | 0.10 | 0.09 | 0.05 |
| E4 | 0.72 | 17.4 | <0.1 | 0.55 | 1.2 | 0.05 | 0.07 | 0.03 |
| E5 | 0.58 | 17 | <0.1 | 0.75 | 1.4 | 0.04 | 0.03 | 0 |
| E6 | 0.55 | 17.6 | <0.1 | 0.70 | 0.95 | 0.09 | 0.05 | 0.09 |
| C1 | 0.41 | 16.2 | 0.8 | 1.46 | 0.95 | <0.01 | 0.002 | 0 |
| C2 | 0.12 | 16.8 | 0.15 | 1.32 | 0.45 | <0.01 | 0.2 | 0 |
| C3 | 0.90 | 17.8 | 0.15 | 0.86 | 1.2 | <0.01 | 0.001 | 0 |

E5: additionally contains 0.006% of B and 0.04% of Nb.

TABLE II

| | 1st Cycle | | | 2nd Cycle | | | 3rd Cycle | | |
|---|---|---|---|---|---|---|---|---|---|
| Alloy | Condensation water test under changing conditions - assessment | AR-30 abrasion [mg] | Overall assessment | Condensation water test under changing conditions - assessment | AR-30 abrasion [mg] | Overall assessment | Condensation water test under changing conditions - assessment | AR-30 abrasion [mg] | Overall assessment |
| A1 | 0 | 1.2 | mottled* | 3 | 4.3 | poor | 3–4 | n.d. | poor |
| A2 | 0–1 | 2 | mottled* | 3–4 | 5.2 | poor | 4 | n.d. | poor |
| A3 | 0–1 | 1.6 | mottled* | 3 | 5.0 | poor | 4–5 | n.d. | poor |
| E1 | 0 | <0.1 | good | 0 | 0.2 | good | 0 | 0.25 | good |
| E2 | 0 | <0.1 | good | 0 | 0.2 | good | 0 | 0.3 | good |
| E3 | 0 | <0.1 | good | 0 | 0.15 | good | 0 | 0.25 | good |
| E4 | 0 | <0.1 | good | 0 | 0.1 | good | 0 | 0.2 | good |
| E5 | 0 | <0.1 | good | 0 | 0.1 | good | 0 | 0.2 | good |
| E6 | 0 | <0.1 | good | 0 | 0.1 | good | 0 | 0.25 | good |
| C1 | 0 | <0.1 | good | 0 | 0.6 | relatively good | 0 | 1.8 | relatively good |
| C2 | 0 | <0.1 | good | 0 | 0.8 | relatively good | 0 | 2.1 | relatively good |

| | | |
|---|---|---|
| Assessment: | 0 | No rust spots |
| Condensation water test under changing conditions | 0–1 | Rust spots at a few locations |
| | 1 | Large numbers of local formations of rust |
| | 1–2 | Continuous spots of rust |
| | 2–4 | 50 to approx. 80% of the surface covered with rust |
| | 4–6 | 80 to 100% of the surface covered with rust |
| Overall assessment: | good: | No significant changes |
| Cycle | relatively good: | Slightly rounded edges and points. |
| | poor: | Considerable wear and rounding of the edge. |
| | mottled*: | Matt areas causes by detachment of the electrodeposition layer | n.d. not determined

Table I compares conventional alloys A1 to A3 and C1 to C3 with six alloys E1 to E6 in accordance with the invention.

These test alloys have been used to carry out tests to determine the overall resistance to wear in a humid atmosphere using the condensation water test under changing conditions as laid down by DIN 50017 together with a subsequent 30-minute or 60-minute chafing test in a rotating vessel. The specimens used were wire pins which had been ground and hardened in the usual way, with a diameter of 1 mm, and industrial needles with a nickel coating applied by electrodeposition. The condensation water test under changing conditions was used to determine the resistance of the specimens to corrosion under these conditions established in a climate chamber. The specimens were stored for 8 hours at 40° C. and 100% relative humidity in air. Then, the specimens were slowly cooled to room temperature over 16 hours and the rust coverage was determined. During the subsequent chafing test, the change in the specimen surface was optically assessed and the mass loss determined.

The bending characteristics of the specimens were determined using an F 33 test machine produced by Shimatzu at a bending rate of 2.5 mm/min. The rigidity S, $F_{max}$ and $S_{max}$ was taken or calculated from the corresponding force/bending diagrams.

The test data are compiled in Tables III and IV below.

TABLE III

| Alloy | K1 | K2 | K3 | $F_{max}$ | $S_{max}$ | S | Comments |
|---|---|---|---|---|---|---|---|
| B1 | 99.6 | 0.022 | 140.0 | 16.9 | 3.2 | 5.3 | Relatively easy to process |
| B2 | 150.0 | 0.029 | 110.0 | 20.0 | 2.0 | 10.0 | Difficult to work |
| B3 | 171.2 | 0.021 | 160.0 | 17.8 | 3.6 | 4.9 | Relatively easy to process |
| E1 | 1.2 | 0.429 | 17.3 | 25.0 | 2.6 | 9.6 | Easy to process |
| E2 | 1.2 | 1.299 | 6.7 | 24.6 | 2.2 | 11.2 | Easy to process |
| E3 | 1.1 | 1.286 | 7.8 | 23.0 | 2.4 | 9.6 | Easy to process |
| E4 | 1.2 | 0.909 | 8.3 | 27.3 | 2.2 | 12.4 | Easy to process |
| E5 | 1.0 | 0.484 | 25.0 | 27.9 | 1.5 | 18.6 | Relatively easy to process Higher heat resistance |
| E6 | 1.0 | 0.781 | 15.8 | 24.3 | 1.7 | 14.3 | Easy to process |
| C1 | 0.7 | 0.048 | 730.0 | 14.0 | 5 | 2.8 | Limited processability |
| C2 | 0.2 | 15.385 | 6.6 | 9.8 | >5 | n.d. | Limited processability |
| C3 | 1.4 | 0.011 | 860.0 | 18.5 | 2.3 | 8.0 | Difficult to process |

E5: additionally contains 0.006% of B and 0.04% of Nb.

TABLE IV

| Alloy | K1 | K2 | K3 | $F_{max}$ | $S_{max}$ | S |
|---|---|---|---|---|---|---|
| A1 | 99.6 | 0.002 | 140 | 16.9 | 3.2 | 5.3 |
| A2 | 152.9 | 0.028 | 110 | 20.0 | 2.0 | 10.0 |
| A3 | 171.2 | 0.021 | 160 | 17.8 | 3.6 | 4.9 |
| E1 | 1.2 | 0.429 | 17.3 | 25.0 | 2.6 | 9.6 |
| E2 | 1.2 | 1.299 | 6.7 | 24.6 | 2.2 | 11.2 |
| E3 | 1.1 | 1.286 | 7.8 | 23.0 | 2.4 | 9.6 |
| E4 | 1.2 | 0.909 | 8.3 | 27.3 | 2.2 | 12.4 |
| E5 | 1.0 | 0.484 | 25.0 | 27.9 | 1.5 | 18.6 |
| E6 | 1.0 | 0.781 | 15.8 | 24.3 | 1.7 | 14.3 |
| C1 | 0.7 | 0.048 | 730 | 14.0 | 5 | 2.8 |
| C2 | 0.2 | 15.385 | 6.6 | 9.8 | >5 | n.d. |
| C3 | 1.4 | 0.011 | 860 | 18.5 | 2.3 | 8.0 |

E5: Comment additionally contains 0.006% of B and 0.04% of Nb.

The data from the two tables demonstrate that the alloys E1 to E6 in accordance with the invention are distinguished by a high rigidity S combined, at the same time, with good processability.

In this connection, the graph illustrates the maximum bending force as a function of the bending, showing the allows E1 to E6 according to the invention compared to the conventional test alloys B1 to B3 and C1 to C3 and known sintered carbides in the tough-hard range.

The range of the invention is indicated by E. It is characterized in that after hardening the needles are in the tough-hard range. B indicates results of tests using a steel containing 0.88% to >1% of carbon. Bi indicates the range of embrittlement caused by hydrogen. In this brittle range, the maximum possible bending force and the bending are greatly reduced.

The range C, by contrast, relates to the characteristics of known stainless steels with a considerable plastic deformation level. In these steels, there is a risk of permanent bending of the needle at high sewing speeds causing considerable damage to the sewing machine.

For comparison purposes, the range D describes the performance of sintered carbide. However, this material is too brittle for practical uses as a needle material.

BRIEF DESCRIPTION OF DRAWING

FIG. 1 shows bending characteristics for different types of prior art steel in comparison to steel of present invention.

As the diagram presented in FIG. 1 shows (cf. also Table III), in the alloy according to the invention the bending characteristic is advantageously kept within tight limits. The advantageous alloy according to the invention for industrial needles (E in FIG. 1) is distinguished by a high alloying content of the matrix, which is advantageously also matched at the same time to the content of carbides, nitrides and carbonitrides.

This matching is defined in particular by the ratios K1, K2 and K3.

Table II shows the results of the wear resistance. A high atmospheric humidity combined with simultaneous abrasion has a particularly unfavorable effect on the overall wear. This double load can be the cause of increased needle wear. Conditions of this type are frequency encountered in particular in tropical countries. Under these conditions, layers applied by electrodeposition offer inadequate protection, since there is increased corrosion after the layer has been removed.

By contrast, the test alloys E1 to E6 according to the invention present only minimal wear under the selected conditions. This is attributable to the fact that, in addition to the matching of the alloying contents, the criteria with regard to factors K1, K2 and K3 are also satisfied, and the matrix is highly wear-resistant.

What is claimed is:

1. A needle for medical and industrial uses made from a chromium steel alloy, having:

| 0.4 to 0.75 | % of carbon |
| 0.4 to 0.8 | % of manganese |
| 14 to 19 | % of chromium |
| up to 0.1 | % of nickel |
| up to 0.4 | % of silicon |
| 0.5 to 1.5 | % of molybdenum |
| 0.05 0.2 | % of vanadium, titanium and niobium |
| 0.025 to 0.15 | of sulfur | remainder iron including smelting-related impurities.

2. The needle of claim 1 wherein said chromium steel alloy contains:

| 0.6 to 0.7 | % of carbon |
| 17 to 19 | % of chromium, |
| 0.03 to 0.1 | % of silicon. |

3. The needle of claim 1 wherein said chromium steel alloy satisfies the following condition $K_1=30\times(\%C+\%N)/(\%Cr+\%Mo)=0.9$ to $1.25$.

4. The needle of claim 1 wherein said chromium steel alloy satisfies the following condition $K_2=10\times S/(\%C+\%N)=0.35$ to $1.50$.

5. The needle of claim 1 wherein said chromium steel alloy satisfies the following condition $K_3(\%Mn+\%Ti)/S=5$ to $30$.

6. The needle of claim 2 wherein said chromium steel alloy satisfies the following condition $K_1=30\times/(\%C+\%N)/(\%Cr+\%Mo)=0.9$ to $1.25$.

7. The needle of claim 2 wherein said chromium steel alloy satisfies the following condition $$K_2 = 10 \times S/(\%C + \%N) = 0.35 \text{ to } 1.50.$$

8. The needle of claim 3 wherein said chromium steel alloy satisfies the following condition $$K_2 = 10 \times S/(\%C + \%N) = 0.35 \text{ to } 1.50.$$

9. The needle of claim 2 wherein said chromium steel alloy satisfies the following condition $$K_3 (\%Mn + \%Ti)/S = 5 \text{ to } 30.$$

10. The needle of claim 3 wherein said chromium steel alloy satisfies the following condition $$K_3 = (\%Mn + \%Ti)/S = 5 \text{ to } 30.$$

11. The needle of claim 4 wherein said chromium steel alloy satisfies the following condition $$K_3 = (\%Mn + \%Ti)/S = 5 \text{ to } 30.$$

* * * * *